(12) United States Patent
McKenna et al.

(10) Patent No.: US 8,423,112 B2
(45) Date of Patent: Apr. 16, 2013

(54) MEDICAL SENSOR AND TECHNIQUE FOR USING THE SAME

(75) Inventors: Edward M. McKenna, Boulder, CO (US); Douglas Paul Miller, Lakewood, CO (US); David Philip Besko, Thorton, CO (US)

(73) Assignee: Covidien LP, Mansfield, MA (US)

( * ) Notice: Subject to any disclaimer, the term of this patent is extended or adjusted under 35 U.S.C. 154(b) by 1233 days.

(21) Appl. No.: 12/242,764

(22) Filed: Sep. 30, 2008

(65) Prior Publication Data

US 2010/0081902 A1 Apr. 1, 2010

(51) Int. Cl.
*A61B 5/1455* (2006.01)

(52) U.S. Cl.
USPC ............ 600/344; 600/322; 600/323; 600/310

(58) Field of Classification Search ........... 600/309–344
See application file for complete search history.

(56) References Cited

U.S. PATENT DOCUMENTS

| | | | |
|---|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |

(Continued)

FOREIGN PATENT DOCUMENTS

| | | |
|---|---|---|
| EP | 1500369 A1 | 1/2005 |
| WO | WO9313706 | 7/1993 |

(Continued)

OTHER PUBLICATIONS

International Search Report PCT/US2009/056965, 4 pages, mailed Nov. 19, 2009.

(Continued)

*Primary Examiner* — Eric Winakur
*Assistant Examiner* — Marjan Fardanesh
(74) *Attorney, Agent, or Firm* — Fletcher Yoder

(57) ABSTRACT

According to embodiments, a medical sensor may be configured for use on mucosal tissue. Such a sensor may include a portion that facilitate the application of the sensor to the tissue and a portion that includes the optical components of the sensor. The two portions of the sensor may be reversibly coupled to one another. In embodiments, such sensors may be used to determine patient hematocrit.

20 Claims, 3 Drawing Sheets

U.S. PATENT DOCUMENTS

| | | | |
|---|---|---|---|
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hausman et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |
| 5,398,680 A | 3/1995 | Polson et al. | |
| 5,402,777 A | 4/1995 | Warring et al. | |
| 5,411,023 A | 5/1995 | Morris, Sr. et al. | |
| 5,411,024 A | 5/1995 | Thomas et al. | |
| 5,413,099 A | 5/1995 | Schmidt et al. | |
| 5,413,100 A | 5/1995 | Barthelemy et al. | |
| 5,413,101 A | 5/1995 | Sugiura | |
| 5,413,102 A | 5/1995 | Schmidt et al. | |
| 5,417,207 A | 5/1995 | Young et al. | |
| 5,421,329 A | 6/1995 | Casciani et al. | |
| 5,425,360 A | 6/1995 | Nelson | |
| 5,425,362 A | 6/1995 | Siker et al. | |
| 5,427,093 A | 6/1995 | Ogawa et al. | |
| 5,429,128 A | 7/1995 | Cadell et al. | |
| 5,429,129 A | 7/1995 | Lovejoy et al. | |
| 5,431,159 A | 7/1995 | Baker et al. | |
| 5,431,170 A | 7/1995 | Mathews | |
| 5,437,275 A | 8/1995 | Amundsen et al. | |
| 5,438,986 A | 8/1995 | Disch et al. | |

| Patent | Date | Name |
|---|---|---|
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,795,304 A | 8/1998 | Sun et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |

| | | | | | | |
|---|---|---|---|---|---|---|
| 5,922,607 | A | 7/1999 | Bernreuter | 6,181,958 B1 | 1/2001 | Steuer et al. |
| 5,924,979 | A | 7/1999 | Swedlow et al. | 6,181,959 B1 | 1/2001 | Schöllermann et al. |
| 5,924,980 | A | 7/1999 | Coetzee | 6,184,521 B1 | 2/2001 | Coffin, IV et al. |
| 5,924,982 | A | 7/1999 | Chin | 6,188,470 B1 | 2/2001 | Grace |
| 5,924,985 | A | 7/1999 | Jones | 6,192,260 B1 | 2/2001 | Chance |
| 5,934,277 | A | 8/1999 | Mortz | 6,195,575 B1 | 2/2001 | Levinson |
| 5,934,925 | A | 8/1999 | Tobler et al. | 6,198,951 B1 | 3/2001 | Kosuda et al. |
| 5,940,182 | A | 8/1999 | Lepper, Jr. et al. | 6,206,830 B1 | 3/2001 | Diab et al. |
| 5,954,050 | A | 9/1999 | Christopher | 6,213,952 B1 | 4/2001 | Finarov et al. |
| 5,954,644 | A | 9/1999 | Dettling et al. | 6,217,523 B1 | 4/2001 | Amano et al. |
| 5,960,610 | A | 10/1999 | Levinson et al. | 6,222,189 B1 | 4/2001 | Misner et al. |
| 5,961,450 | A | 10/1999 | Merchant et al. | 6,226,539 B1 | 5/2001 | Potratz |
| 5,961,452 | A | 10/1999 | Chung et al. | 6,226,540 B1 | 5/2001 | Bernreuter et al. |
| 5,964,701 | A | 10/1999 | Asada et al. | 6,229,856 B1 | 5/2001 | Diab et al. |
| 5,971,930 | A | 10/1999 | Elghazzawi | 6,230,035 B1 | 5/2001 | Aoyagi et al. |
| 5,978,691 | A | 11/1999 | Mills | 6,233,470 B1 | 5/2001 | Tsuchiya |
| 5,978,693 | A | 11/1999 | Hamilton et al. | 6,236,871 B1 | 5/2001 | Tsuchiya |
| 5,983,122 | A | 11/1999 | Jarman et al. | 6,236,872 B1 | 5/2001 | Diab et al. |
| 5,987,343 | A | 11/1999 | Kinast | 6,240,305 B1 | 5/2001 | Tsuchiya |
| 5,991,648 | A | 11/1999 | Levin | 6,253,097 B1 | 6/2001 | Aronow et al. |
| 5,995,855 | A | 11/1999 | Kiani et al. | 6,253,098 B1 | 6/2001 | Walker et al. |
| 5,995,856 | A | 11/1999 | Mannheimer et al. | 6,256,523 B1 | 7/2001 | Diab et al. |
| 5,995,858 | A | 11/1999 | Kinast | 6,256,524 B1 | 7/2001 | Walker et al. |
| 5,995,859 | A | 11/1999 | Takahashi | 6,261,236 B1 | 7/2001 | Grimblatov |
| 5,997,343 | A | 12/1999 | Mills et al. | 6,263,221 B1 | 7/2001 | Chance et al. |
| 5,999,834 | A | 12/1999 | Wang et al. | 6,263,222 B1 | 7/2001 | Diab et al. |
| 6,002,952 | A | 12/1999 | Diab et al. | 6,263,223 B1 | 7/2001 | Shepherd et al. |
| 6,005,658 | A | 12/1999 | Kaluza et al. | 6,266,546 B1 | 7/2001 | Steuer et al. |
| 6,006,119 | A * | 12/1999 | Soller et al. ............... 600/322 | 6,266,547 B1 | 7/2001 | Walker et al. |
| 6,006,120 | A | 12/1999 | Levin | 6,272,363 B1 | 8/2001 | Casciani et al. |
| 6,011,985 | A | 1/2000 | Athan et al. | 6,278,522 B1 | 8/2001 | Lepper, Jr. et al. |
| 6,011,986 | A | 1/2000 | Diab et al. | 6,280,213 B1 | 8/2001 | Tobler et al. |
| 6,014,576 | A | 1/2000 | Raley et al. | 6,280,381 B1 | 8/2001 | Malin et al. |
| 6,018,673 | A | 1/2000 | Chin et al. | 6,285,894 B1 | 9/2001 | Oppelt et al. |
| 6,018,674 | A | 1/2000 | Aronow | 6,285,895 B1 | 9/2001 | Ristolainen et al. |
| 6,022,321 | A | 2/2000 | Amano et al. | 6,285,896 B1 | 9/2001 | Tobler et al. |
| 6,023,541 | A | 2/2000 | Merchant et al. | 6,298,252 B1 | 10/2001 | Kovach et al. |
| 6,026,312 | A | 2/2000 | Shemwell et al. | 6,308,089 B1 | 10/2001 | Von der Ruhr et al. |
| 6,026,314 | A | 2/2000 | Amerov et al. | 6,309,352 B1 | 10/2001 | Oraevsky et al. |
| 6,031,603 | A | 2/2000 | Fine et al. | 6,321,100 B1 | 11/2001 | Parker |
| 6,035,223 | A | 3/2000 | Baker, Jr. | 6,330,468 B1 | 12/2001 | Scharf |
| 6,036,642 | A | 3/2000 | Diab et al. | 6,334,065 B1 | 12/2001 | Al-Ali et al. |
| 6,041,247 | A | 3/2000 | Weckstrom et al. | 6,339,715 B1 | 1/2002 | Bahr et al. |
| 6,044,283 | A | 3/2000 | Fein et al. | 6,343,223 B1 | 1/2002 | Chin et al. |
| 6,047,201 | A | 4/2000 | Jackson, III | 6,343,224 B1 | 1/2002 | Parker |
| 6,061,584 | A | 5/2000 | Lovejoy et al. | 6,349,228 B1 | 2/2002 | Kiani et al. |
| 6,064,898 | A | 5/2000 | Aldrich | 6,351,658 B1 | 2/2002 | Middleman et al. |
| 6,064,899 | A | 5/2000 | Fein et al. | 6,353,750 B1 | 3/2002 | Kimura et al. |
| 6,067,462 | A | 5/2000 | Diab et al. | 6,356,774 B1 | 3/2002 | Bernstein et al. |
| 6,073,038 | A | 6/2000 | Wang et al. | 6,360,113 B1 | 3/2002 | Dettling |
| 6,078,833 | A | 6/2000 | Hueber | 6,360,114 B1 | 3/2002 | Diab et al. |
| 6,081,735 | A | 6/2000 | Diab et al. | 6,361,501 B1 | 3/2002 | Amano et al. |
| 6,081,742 | A | 6/2000 | Amano et al. | 6,363,269 B1 | 3/2002 | Hanna et al. |
| 6,083,157 | A | 7/2000 | Noller | 6,370,408 B1 | 4/2002 | Merchant et al. |
| 6,083,172 | A | 7/2000 | Baker, Jr. et al. | 6,370,409 B1 | 4/2002 | Chung et al. |
| 6,088,607 | A | 7/2000 | Diab et al. | 6,374,129 B1 | 4/2002 | Chin et al. |
| 6,094,592 | A | 7/2000 | Yorkey et al. | 6,377,829 B1 | 4/2002 | Al-Ali et al. |
| 6,095,974 | A | 8/2000 | Shemwell et al. | 6,381,479 B1 | 4/2002 | Norris |
| 6,104,938 | A | 8/2000 | Huiku et al. | 6,381,480 B1 | 4/2002 | Stoddart et al. |
| 6,112,107 | A | 8/2000 | Hannula | 6,385,471 B1 | 5/2002 | Mortz |
| 6,113,541 | A | 9/2000 | Dias et al. | 6,385,821 B1 | 5/2002 | Modgil et al. |
| 6,115,621 | A | 9/2000 | Chin | 6,388,240 B2 | 5/2002 | Schulz et al. |
| 6,122,535 | A | 9/2000 | Kaestle et al. | 6,393,310 B1 | 5/2002 | Kuenstner |
| 6,133,994 | A | 10/2000 | Mathews et al. | 6,397,091 B2 | 5/2002 | Diab et al. |
| 6,135,952 | A | 10/2000 | Coetzee | 6,397,092 B1 | 5/2002 | Norris et al. |
| 6,144,444 | A | 11/2000 | Haworth et al. | 6,397,093 B1 | 5/2002 | Aldrich |
| 6,144,867 | A | 11/2000 | Walker et al. | 6,400,971 B1 | 6/2002 | Finarov et al. |
| 6,144,868 | A | 11/2000 | Parker | 6,400,972 B1 | 6/2002 | Fine |
| 6,149,481 | A | 11/2000 | Wang et al. | 6,402,690 B1 | 6/2002 | Rhee et al. |
| 6,150,951 | A | 11/2000 | Olejniczak | 6,408,198 B1 | 6/2002 | Hanna et al. |
| 6,151,107 | A | 11/2000 | Schöllermann et al. | 6,411,832 B1 | 6/2002 | Guthermann |
| 6,151,518 | A | 11/2000 | Hayashi | 6,411,833 B1 | 6/2002 | Baker, Jr. et al. |
| 6,152,754 | A | 11/2000 | Gerhardt et al. | 6,419,671 B1 | 7/2002 | Lemberg |
| 6,154,667 | A | 11/2000 | Miura et al. | 6,421,549 B1 | 7/2002 | Jacques |
| 6,163,175 | A | 12/2000 | Larsen et al. | 6,430,423 B2 | 8/2002 | DeLonzor et al. |
| 6,163,715 | A | 12/2000 | Diab et al. | 6,430,513 B1 | 8/2002 | Wang et al. |
| 6,165,005 | A | 12/2000 | Mills et al. | 6,430,525 B1 | 8/2002 | Weber et al. |
| 6,173,196 | B1 | 1/2001 | Delonzor et al. | 6,434,408 B1 | 8/2002 | Heckel et al. |
| 6,178,343 | B1 | 1/2001 | Bindszus et al. | 6,438,399 B1 | 8/2002 | Kurth |

| Patent | Date | Inventor |
|---|---|---|
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,711,426 B2 | 3/2004 | Benaron et al. |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B2 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |

| | | | | | | |
|---|---|---|---|---|---|---|
| 6,830,711 B2 | 12/2004 | Mills et al. | | 7,162,288 B2 | 1/2007 | Nordstrom |
| 6,836,679 B2 | 12/2004 | Baker, Jr. et al. | | 7,190,987 B2 | 3/2007 | Lindekugel et al. |
| 6,839,579 B1 | 1/2005 | Chin | | 7,201,734 B2 | 4/2007 | Hickle |
| 6,839,580 B2 | 1/2005 | Zonios et al. | | 7,209,775 B2 | 4/2007 | Bae et al. |
| 6,839,582 B2 | 1/2005 | Heckel | | 7,215,984 B2 | 5/2007 | Diab et al. |
| 6,839,659 B2 | 1/2005 | Tarassenko et al. | | 7,225,006 B2 | 5/2007 | Al-Ali et al. |
| 6,842,635 B1 | 1/2005 | Parker | | 7,236,811 B2 | 6/2007 | Schmitt |
| 6,845,256 B2 | 1/2005 | Chin et al. | | 7,247,154 B2 | 7/2007 | Hickle |
| 6,850,787 B2 | 2/2005 | Weber et al. | | 7,248,910 B2 | 7/2007 | Li et al. |
| 6,850,788 B2 | 2/2005 | Al-Ali | | 7,254,433 B2 | 8/2007 | Diab et al. |
| 6,850,789 B2 | 2/2005 | Schweitzer, Jr. et al. | | 7,254,434 B2 | 8/2007 | Schulz et al. |
| 6,855,116 B2 | 2/2005 | Atlee | | 7,263,395 B2 | 8/2007 | Chan et al. |
| 6,861,639 B2 | 3/2005 | Al-Ali | | 7,272,426 B2 | 9/2007 | Scmid |
| 6,863,652 B2 | 3/2005 | Huang et al. | | 7,280,858 B2 | 10/2007 | Al-Ali et al. |
| 6,865,407 B2 | 3/2005 | Kimball et al. | | 7,295,866 B2 | 11/2007 | Al-Ali et al. |
| 6,878,118 B2 | 4/2005 | Atlee | | 7,305,262 B2 | 12/2007 | Brodnick et al. |
| 6,879,850 B2 | 4/2005 | Kimball | | 7,315,753 B2 | 1/2008 | Baker, Jr. et al. |
| 6,882,874 B2 | 4/2005 | Huiku | | 7,330,746 B2 | 2/2008 | Demuth et al. |
| 6,889,153 B2 | 5/2005 | Dietiker | | 7,349,726 B2 | 3/2008 | Casciani et al. |
| 6,898,452 B2 | 5/2005 | Al-Ali et al. | | 7,376,454 B2 | 5/2008 | Casciani et al. |
| 6,909,912 B2 | 6/2005 | Melker et al. | | 7,415,298 B2 | 8/2008 | Casciani et al. |
| 6,912,413 B2 | 6/2005 | Rantala et al. | | 7,430,444 B2 | 9/2008 | Pologe et al. |
| 6,916,289 B2 | 7/2005 | Schnall | | 7,440,788 B2 | 10/2008 | Jenkins et al. |
| 6,920,345 B2 | 7/2005 | Al-Ali et al. | | 2001/0021803 A1 | 9/2001 | Blank et al. |
| 6,931,269 B2 | 8/2005 | Terry | | 2001/0051767 A1 | 12/2001 | Williams et al. |
| 6,934,570 B2 | 8/2005 | Kiani et al. | | 2002/0026109 A1 | 2/2002 | Diab et al. |
| 6,939,307 B1 | 9/2005 | Dunlop | | 2002/0028990 A1 | 3/2002 | Shepherd et al. |
| 6,941,162 B2 | 9/2005 | Fudge et al. | | 2002/0038078 A1 | 3/2002 | Ito |
| 6,947,781 B2 | 9/2005 | Asada et al. | | 2002/0042558 A1 | 4/2002 | Mendelson |
| 6,950,687 B2 | 9/2005 | Al-Ali | | 2002/0068859 A1 | 6/2002 | Knopp |
| 6,961,600 B2 | 11/2005 | Kohl et al. | | 2002/0082489 A1 | 6/2002 | Casciani et al. |
| 6,963,767 B2 | 11/2005 | Rantala et al. | | 2002/0128544 A1 | 9/2002 | Diab et al. |
| 6,971,580 B2 | 12/2005 | DeLonzor et al. | | 2002/0133067 A1 | 9/2002 | Jackson, III |
| 6,983,178 B2 | 1/2006 | Fine et al. | | 2002/0156354 A1 | 10/2002 | Larson |
| 6,985,763 B2 | 1/2006 | Boas et al. | | 2002/0173706 A1 | 11/2002 | Takatani |
| 6,985,764 B2 | 1/2006 | Mason et al. | | 2002/0173709 A1 | 11/2002 | Fine et al. |
| 6,990,426 B2 | 1/2006 | Yoon et al. | | 2002/0190863 A1 | 12/2002 | Lynn |
| 6,992,751 B2 | 1/2006 | Al-Ali et al. | | 2002/0198442 A1 | 12/2002 | Rantala et al. |
| 6,992,772 B2 | 1/2006 | Block et al. | | 2003/0018243 A1 | 1/2003 | Gerhardt et al. |
| 6,993,371 B2 | 1/2006 | Kiani et al. | | 2003/0036690 A1 | 2/2003 | Geddes et al. |
| 6,993,372 B2 | 1/2006 | Fine et al. | | 2003/0045785 A1 | 3/2003 | Diab et al. |
| 6,996,427 B2 | 2/2006 | Ali et al. | | 2003/0073889 A1 | 4/2003 | Keilbach et al. |
| 7,003,338 B2 | 2/2006 | Weber et al. | | 2003/0073890 A1 | 4/2003 | Hanna |
| 7,003,339 B2 | 2/2006 | Diab et al. | | 2003/0100840 A1 | 5/2003 | Sugiura et al. |
| 7,006,855 B1 | 2/2006 | Sarussi | | 2003/0132495 A1 | 7/2003 | Mills et al. |
| 7,006,856 B2 | 2/2006 | Baker, Jr. et al. | | 2003/0135099 A1 | 7/2003 | Al-Ali |
| 7,016,715 B2 | 3/2006 | Stetson | | 2003/0144584 A1 | 7/2003 | Mendelson |
| 7,020,507 B2 | 3/2006 | Scharf et al. | | 2003/0162414 A1 | 8/2003 | Schulz et al. |
| 7,024,233 B2 | 4/2006 | Ali et al. | | 2003/0171662 A1 | 9/2003 | O'Connor et al. |
| 7,024,235 B2 | 4/2006 | Melker et al. | | 2003/0176776 A1 | 9/2003 | Huiku |
| 7,025,728 B2 | 4/2006 | Ito et al. | | 2003/0181797 A1 | 9/2003 | Kohl et al. |
| 7,027,849 B2 | 4/2006 | Al-Ali et al. | | 2003/0181799 A1 | 9/2003 | Lindekugel et al. |
| 7,027,850 B2 | 4/2006 | Wasserman | | 2003/0187337 A1 | 10/2003 | Tarassenko et al. |
| 7,035,697 B1 | 4/2006 | Brown | | 2003/0195402 A1 | 10/2003 | Fein et al. |
| 7,039,449 B2 | 5/2006 | Al-Ali | | 2003/0197679 A1 | 10/2003 | Ali et al. |
| 7,043,289 B2 | 5/2006 | Fine et al. | | 2003/0212316 A1 | 11/2003 | Leiden et al. |
| 7,047,055 B2 | 5/2006 | Boas et al. | | 2003/0225323 A1 | 12/2003 | Kiani et al. |
| 7,047,056 B2 | 5/2006 | Hannula et al. | | 2003/0225337 A1 | 12/2003 | Scharf et al. |
| 7,060,035 B2 | 6/2006 | Wasserman et al. | | 2003/0236452 A1 | 12/2003 | Melker et al. |
| 7,062,306 B2 | 6/2006 | Benaron et al. | | 2003/0236647 A1 | 12/2003 | Yoon et al. |
| 7,062,307 B2 | 6/2006 | Norris et al. | | 2004/0006261 A1 | 1/2004 | Swedlow et al. |
| 7,067,893 B2 | 6/2006 | Mills et al. | | 2004/0010188 A1 | 1/2004 | Wasserman |
| 7,072,701 B2 | 7/2006 | Chen et al. | | 2004/0024297 A1 | 2/2004 | Chen et al. |
| 7,072,702 B2 | 7/2006 | Edgar, Jr. et al. | | 2004/0024326 A1 | 2/2004 | Yeo et al. |
| 7,079,880 B2 | 7/2006 | Stetson | | 2004/0034293 A1 | 2/2004 | Kimball |
| 7,085,597 B2 | 8/2006 | Fein et al. | | 2004/0039272 A1 | 2/2004 | Abdul-Hafiz et al. |
| 7,090,648 B2 | 8/2006 | Sackner et al. | | 2004/0039273 A1 | 2/2004 | Terry |
| 7,096,052 B2 | 8/2006 | Mason et al. | | 2004/0054269 A1 | 3/2004 | Rantala et al. |
| 7,096,054 B2 | 8/2006 | Abdul-Hafiz et al. | | 2004/0054291 A1 | 3/2004 | Schulz et al. |
| 7,103,402 B2 | 9/2006 | Vo-Dinh | | 2004/0059209 A1 | 3/2004 | Al-Ali et al. |
| 7,107,088 B2 | 9/2006 | Aceti | | 2004/0059210 A1 | 3/2004 | Stetson |
| 7,113,815 B2 | 9/2006 | O'Neil et al. | | 2004/0064020 A1 | 4/2004 | Diab et al. |
| 7,123,950 B2 | 10/2006 | Mannheimer | | 2004/0068164 A1 | 4/2004 | Diab et al. |
| 7,127,278 B2 | 10/2006 | Melker et al. | | 2004/0087846 A1 | 5/2004 | Wasserman |
| 7,130,671 B2 | 10/2006 | Baker, Jr. et al. | | 2004/0092805 A1 | 5/2004 | Yarita |
| 7,132,641 B2 | 11/2006 | Schulz et al. | | 2004/0097797 A1 | 5/2004 | Porges et al. |
| 7,133,711 B2 | 11/2006 | Chernoguz et al. | | 2004/0098009 A1 | 5/2004 | Boecker et al. |
| 7,139,599 B2 | 11/2006 | Terry | | 2004/0107065 A1 | 6/2004 | Al-Ali |
| 7,142,901 B2 | 11/2006 | Kiani et al. | | 2004/0116788 A1 | 6/2004 | Chernoguz et al. |

| Publication No. | Date | Inventor |
|---|---|---|
| 2004/0116789 A1 | 6/2004 | Boas et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0182389 A1 | 8/2005 | Laporte et al. |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0020179 A1 | 1/2006 | Anderson et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195026 A1 | 8/2006 | Casciani et al. |
| 2006/0195027 A1 | 8/2006 | Casciani et al. |
| 2006/0195028 A1 | 8/2006 | Hannula et al. |
| 2006/0211929 A1 | 9/2006 | Casciani et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0276697 A1 | 12/2006 | Demuth et al. |
| 2006/0276700 A1 | 12/2006 | O'Neil |
| 2007/0027375 A1 | 2/2007 | Melker et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0038126 A1 | 2/2007 | Pyle et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0078318 A1 | 4/2007 | Kling et al. |
| 2007/0118045 A1 | 5/2007 | Naghavi et al. |
| 2008/0009689 A1 | 1/2008 | Benaron et al. |
| 2008/0021379 A1 | 1/2008 | Hickle |
| 2008/0188727 A1 | 8/2008 | Benaron et al. |
| 2008/0262418 A1 | 10/2008 | Burnett et al. |
| 2008/0287758 A1 | 11/2008 | Benaron et al. |

FOREIGN PATENT DOCUMENTS

| | | |
|---|---|---|
| WO | WO9851212 | 11/1998 |
| WO | WO9947039 | 9/1999 |
| WO | WO0117421 | 3/2001 |
| WO | WO 0187151 A2 | 11/2001 |
| WO | WO2005025399 | 3/2005 |
| WO | WO 2006020956 A2 | 2/2006 |
| WO | WO 2006086010 A2 | 8/2006 |
| WO | WO2007041331 | 4/2007 |
| WO | WO2008019294 | 2/2008 |
| WO | WO2008020845 | 2/2008 |

OTHER PUBLICATIONS

Hemametrics, Crit-Line III-TQA a Fluid Management and Access Monitoring Tool, http://www.hemametrics.com/main.jsp?page=productInfoContent.jsp&Id=1; 1 pages (last viewed Aug. 24, 2011).

Hemametrics, Crit-Line Technology to Blood Flow Monitors and Oxygen Monitoring, http://www.hemametrics.com/main.jsp?page=technologyContent.jsp; 1 page (last viewed Aug. 24, 2011).

Hemametrics, Crit-Line Fluid Management Device for Hemodialysis, http://www.hemametrics.com/main.jsp?page=doctorsContent.jsp; 1 page (last viewed Aug. 24, 2011).

Zhang, S., et al. "Investigation of Noninvasive in Vivo Blood Hematocrit Measurement Using NIR Reflectance Spectroscopy and Partial Least-Squares Regression", Applied Spectroscopy, vol. 54, No. 2, pp. 294-299 (2000).

Nadeau, R., et al. "Innovative Non- or Minimally-Invasive Technologies for Monitoring Health and Nutritional Status in Mothers and Young Children"; American Society for Nutritional Sciences, In The Journal of Nutrition, 131: 1610S-1614S (2001).

Jeon, K., et al. "Noninvasive total hemoglobin measurement"; Journal of Biomedical Optics, vol. 7, No. 1, pp. 45-50 (Jan. 2002).

Soller, B., et al. "Smart Medical Systems With Application to Nutrition and Fitness in Space"; Nutrition: 18:930-936 (2002).

Aldrich, T., et al. "Length-Normalized Pulse Photoplethysmography: A Noninvasive Method to Measure Blood Hemoglobin"; Annals of Biomedical Engineering, vol. 30, pp. 1291-1298 (2002).

Kukreti, S., et al. "Intrinsic tumor biomarkers revealed by novel double-differential spectroscopic analysis of near-infrared spectra"; JBO Letters, Journal of Biomedical Optics, vol. 12(2), pp. 020509-1-020509-3 (Mar./Apr. 2007).

McCurdy, J., et al. "Noninvasive Optical, Electrical, and Acoustic Methods of Total Hemoglobin Determination"; Reviews, Clinical Chemistry 54:2, 264-272 (2008).

Weil, Max Harry, et al.; "Sublingual Capnometry: A New Noninvasive Measurement for Diagnosis and Quantitation of Severity of Circulatory Shock"; Cirtical Care Medicine, vol. 27, No. 7 (1999).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

US 4,928,691, 05/1990, Nicolson et al. (withdrawn)

* cited by examiner

MEDICAL SENSOR AND TECHNIQUE FOR USING THE SAME

BACKGROUND

The present disclosure relates generally to medical devices and, more particularly, to sensors used for sensing physiological parameters of a patient.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

A physiological characteristic that may provide information about the clinical condition of a patient is the total concentration of hemoglobin in blood ($Hb_T$) or the hematocrit (Hct), which relates to the fraction or percentage of red cells in whole blood. The hematocrit is the fraction of the total blood volume occupied by the red blood cells, and hemoglobin is the principal active constituent of red blood cells. Approximately 34% of the red cell volume is occupied by hemoglobin.

Measurements of a patient's hematocrit (Hct) levels may involve an invasive technique. For example, a healthcare provider may puncture the skin, draw blood from a vein or capillary into a small-diameter tube, and measure the solid (packed-cell) fraction that remains after centrifugation of the blood. Similarly, measurement of $Hb_T$ in often may involve a healthcare worker drawing a blood sample, which is then subjected to a chemical or mechanical process to lyse the red cells and release the liquid hemoglobin. After transferring the hemoglobin to a cuvette, its concentration may be measured either by direct spectrophotometry or by colorimetry, following the addition of a chemical reagent. Both of these techniques are relatively labor-intensive, as they involve the participation of skilled healthcare workers in drawing the blood and skilled laboratory workers to perform the subsequent analysis.

Certain noninvasive methods for measurement of hematocrit or total hemoglobin concentration involve spectrophotometric measurement of blood in intact skin. The method is based in part on the measurement of the ratios of the pulsatile (AC) and non-pulsatile (DC) components of the light transmitted through a blood-perfused tissue within two spectral bands in which the molar extinction coefficients of oxygenated hemoglobin ($HbO_2$) and deoxygenated hemoglobin (Hb) are nearly the same. In one of the wavelength bands, the absorption of hemoglobin is the dominant contributor to the attenuation of light in blood; in the other band, the scattering and absorption of surrounding tissue constituents dominates. Therefore, the scattering and absorption of surrounding tissue constituents serves as a measure of the probed volume in the tissue bed.

In spite of the use of noninvasive techniques, measuring the absolute concentration of hemoglobin in blood accurately and reliably remains difficult in practice. Areas of low perfusion may generate measurement signals that are overwhelmed by the scattering and absorption of surrounding tissues. In addition, variable pulsatile changes in blood volume may introduce measurement variability.

BRIEF DESCRIPTION OF THE DRAWINGS

Advantages of the disclosure may become apparent upon reading the following detailed description and upon reference to the drawings in which.

DETAILED DESCRIPTION

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with embodiments, medical sensors for spectroscopically measuring hematocrit or other physiological parameters are provided that are configured to be applied to mucosal tissue surfaces of a patient. For example, sensors are provided that include an attachment portion adapted to secure the sensor to the mucosal surface. In embodiment, the sensors may also include a removable optical portion that contains the optical components of the sensor. In one embodiment, the emitted light from the optical components may be delivered through the attachment portion to the mucosal tissue. In turn, the light reflected back from the emitter may be delivered through the attachment portion of the sensor to impinge the detector, which may generate a signal related to the physiological parameter of interest.

Mucosal tissue may be well suited for determination of patient hematocrit levels because of the presence of near surface capillary beds that are well-perfused and contain little pulsatility. Sensors for determining hematocrit as provided herein may include optical components that are spaced apart at a distance that allows shallow penetration of mucosal tissue. In embodiments, the emitted light penetrates into the interrogated mucosal tissue with a mean penetration depth of less than 2 mm. This shallow penetration may provide a signal generated at a detector that is enriched in information related to the patient hematocrit and that minimizes strong absorption by tissue components not related to hematocrit levels.

Figure 1:
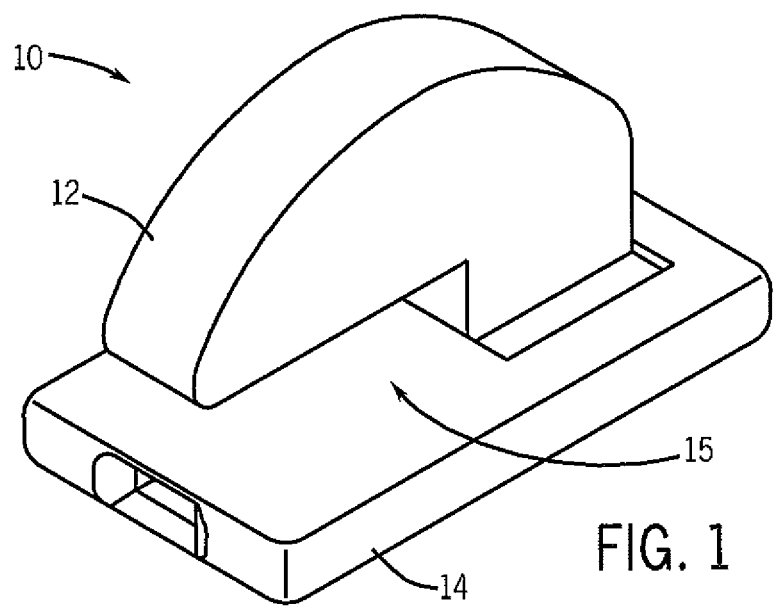
FIG. 1 illustrates a perspective view of an exemplary sensor for holding a medical sensor on a patient's mucosal tissue.

FIG. 1 illustrates an exemplary embodiment of a hematocrit sensor 10 including an attachment portion 12. Sensor optical components are located in an optical portion 14. Both the attachment portion 12 and the optical portion 14 may be made from any suitable material. In one embodiment, the attachment portion 12 and optical portion 14 may be made from rigid or semi-rigid polymeric materials. In one embodiment, the attachment portion 12 and/or the optical portion 14 may include a conformable coating that may include few or generally no sharp edges that may be uncomfortable for a patient.

Figure 2:
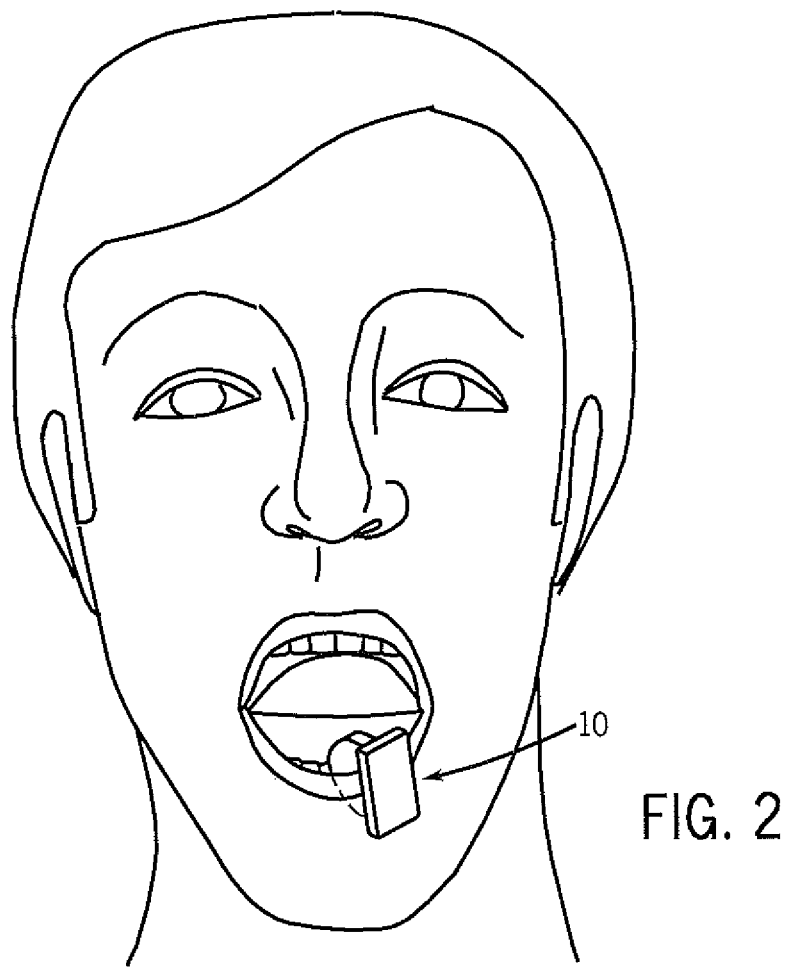
FIG. 2 illustrates a view of the sensor of FIG. 1 applied to a patient's lip.

The attachment portion 12 may be in a hook configuration that is adapted to be placed over the lip of a patient as shown in FIG. 2. For example, a healthcare provider may apply the sensor 10 to the lip by placing the lip tissue inside the open portion 15 of the hook. In embodiments, the sensor 10 may be nonadhesively applied to the tissue In an embodiment, the attachment of the sensor 10 to the tissue may be augmented by the use of one or more mucoadhesive compounds. It is envisioned that the open portion 15 of the hook may be sized and shaped to allow the lip to fit easily within the space without undue mechanical compression. In certain embodiments, the sensor 10 may be configured so that the attachment portion 12 and the optical portion 14 have a slight bias towards one another. In such embodiments, the lip tissue may be slightly compressed within the sensor 10. This compression may have the effect of producing a larger blood volume change, which in one embodiment may increase the amplitude of pulsatile changes. In addition, a slight bias may increase the attachment force of the sensor 10 to the lip. In other embodiments, the attachment portion 12 may be in any suitable shape to apply the sensor 10 to a mucosal tissue of a patient. For example, the attachment portion 12 and the optical portion 14 may form a clip to capture buccal tissue on the inside of the cheek. In other embodiments, the attachment portion 12 hook or clip piece may be somewhat elongated relative to the optical portion 14. In such embodiment, the sensor 10 may be applied to the nose of a patient and the elongated attachment portion 12 may extend into the nose to directly contact nasal mucosal tissue. In embodiments, an attachment portion 12 may include a multi-pronged hook piece that may increase the contact area with the mucosal tissue, and, as a result, increase the attachment strength of the sensor 10.

Figure 3:
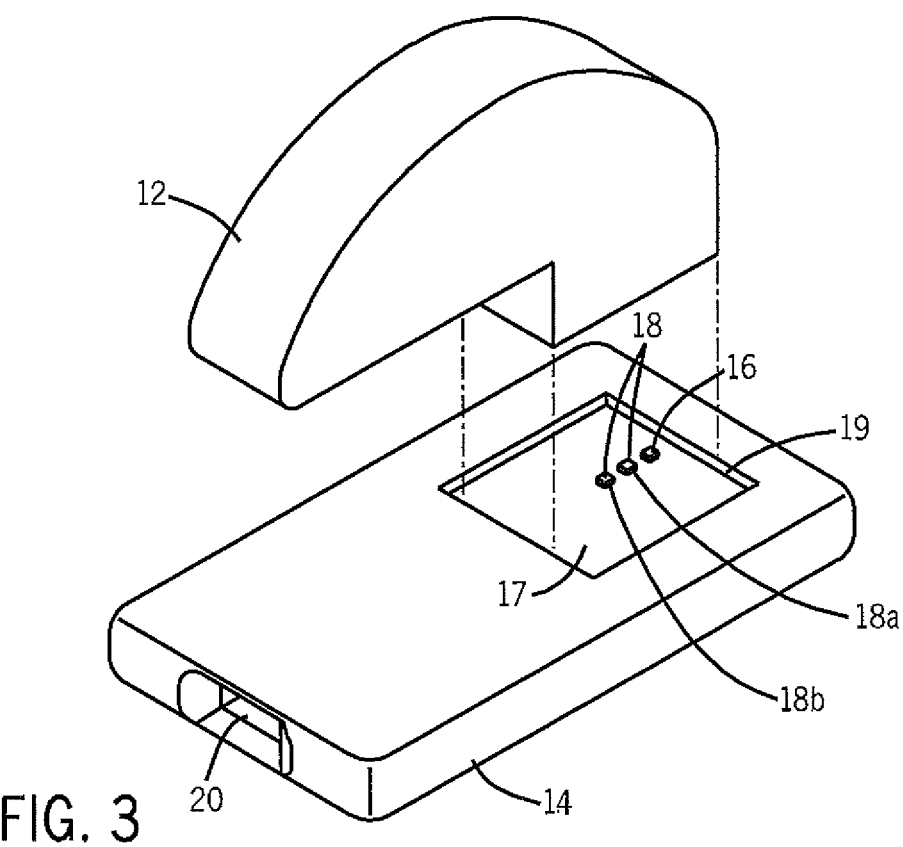
FIG. 3 illustrates a perspective view of the sensor of FIG. 1 with an hook portion detached from a portion holding optical components.

FIG. 3 depicts a view in which the attachment portion 12 is reversibly detached from the optical portion 14. As shown, the attachment portion may clip into grooves 19 shown on the optical portion 14. In such an embodiment, the attachment portion 12 may include corresponding tongues configured to mate with grooves 19. In other embodiments, the attachment portion 12 may be attached to the optical portion 14 by any suitable mechanism, which may include clips, magnetic attachments, snaps, and/or hook and loop closures. In embodiments, an optical portion 14 may be configured to mate with a variety of differently configured attachment portions 12 that may be selected based on the patient's age or size, or the tissue monitoring location.

Also shown in FIG. 3 are optical components including light emitter 16 and light detectors 18. The optical components may be surrounded by a substrate 17 is black or dark in color to absorb stray light and minimize any release of emitted light through openings between the attachment portion 12 and the optical portion 14. In addition, the optical components may be slightly inset from the surface of the optical portion 14 to further decrease the amount of light lost to the environment.

In one embodiment, the sensor 10 may include an emitter 16 containing emitters for two or more wavelengths of light and two detectors 18 spaced apart from the emitter 16 that are configured to detected the respective two wavelengths of light. As shown here, the emitter 16 and the detectors 18 are on an axis with a first detectors 18a being spaced closer to the emitter than a second detectors 18b. However, other configurations including any number of emitters 16 and detectors 18 are also envisioned. For example, the emitter 16 may be in between two detectors 18 so that the distance between the emitter 16 and the detectors 18 is substantially equal. In one embodiment, the detectors are spaced in a range of about 1 mm to about 2.5 mm or about 2 mm to about 2.5 mm apart from the detector. Such an emitter-detector spacing distance may be appropriate for penetrating into shallow capillary beds, such as those found in the lip.

Also shown in FIG. 3 is a cable port 20 that may provide electrical connection to a downstream monitor to providing drive current to the emitter and providing the detector signal to the medical device, according to an embodiment. In addition to providing the electrical connection to the downstream medical device, the cable may provide shielding to protect the signals from the detector against external electrical interference. In embodiments, the cable port 20 may be a universal serial bus (USB) port that is adapted to receive a USB cable that may also contain a compatible end to connect to a downstream medical monitor.

Figure 4:
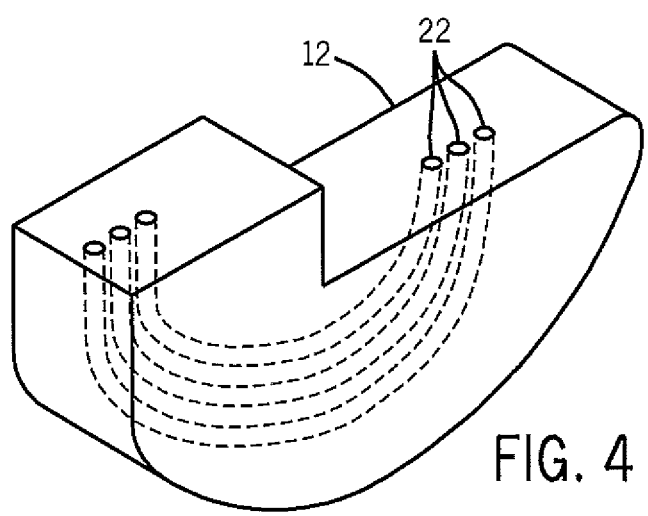
FIG. 4 illustrates a perspective view of an exemplary hook portion.

In embodiments, the emitter 16 and the detectors 18 may be remotely located and optically coupled to the sensor assembly 10 using light pipes or optical fibers. FIG. 4 illustrates a view of the attachment portion 12 including light pipes 22 for transmitting light from the emitter 16 into a patient's tissue. In an embodiment, the attachment portion 12 may include one or more light pipes 22 (e.g., optical fiber bundles) that correspond to the position of each of the emitters 16 and detectors 18. When the attachment portion is connected to the optical portion, the light pipes 22 may transmit the emitted light from the emitter 16 into the tissue and may transmit emitted light that has passed through the tissue to the detectors 18. An additional advantage provided by this sensor configuration is the isolation of the optical components from the relatively aqueous environment of the mucosal tissue. Accordingly, in embodiments, the more electrically and mechanically complex optical portion 14 may be reusable in other applications while a relatively inexpensive attachment portion may be discarded after use.

Figure 5:
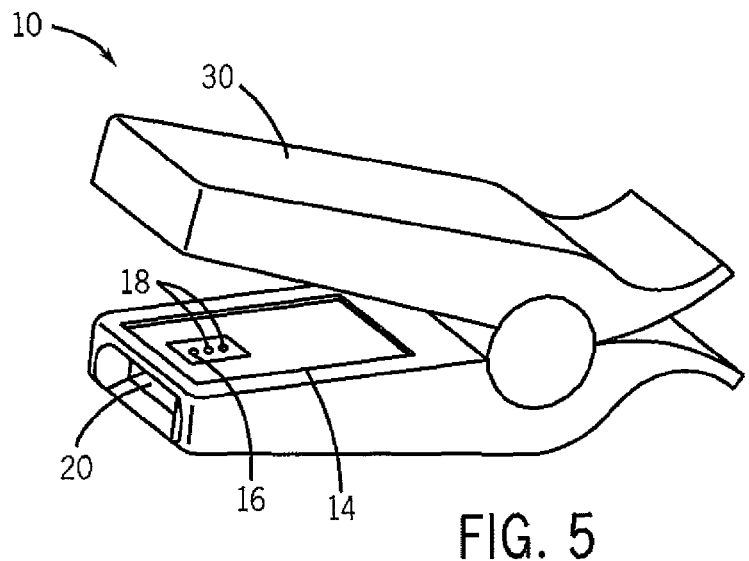
FIG. 5 is a side view of an exemplary clip-style sensor including a removable portion holding optical components.

For example, FIG. 5 illustrates an exemplary finger clip sensor 10, such as a pulse oximetry sensor. A clip-style sensor body 30 may include an inset portion suitably sized and shaped to accommodate the optical portion 14. After use in a lip sensor, the optical portion 14 may be clipped off a lip attachment portion 12 and snapped into a clip-style sensor body 30. The sensor body 30 may also include an opening allowing access to cable port 20 in the optical portion 14. In one embodiment, the optical portion 14 may be used to collect monitoring data for determining hematocrit while connected to an attachment portion 12. The optical portion 14 may also be snapped into a sensor body 30 that is configured to clip onto a patient's digit and collect pulse oximetry data. In one embodiment, the sensor body 30 includes an encoder or other element that is connected or activated upon insertion of the optical portion to provide instructions to the downstream monitor to run routines associated with processing oximetry data. In one embodiment, the optical portion may include an emitter 16 and detectors 18 set appropriate for monitoring hematocrit levels and an alternative emitter 16 and detectors 18 set that may be configured to emit light and detect light at wavelengths compatible with pulse oximetry monitoring. When the optical portion is snapped into a sensor body compatible for pulse oximetry, the optical portion 14 may be adapted to use the pulse oximetry emitter 16 and detectors 18 set. For example, in one embodiment, a user may select "PULSE OXIMETRY" or "HEMATOCRIT" from a menu on a downstream medical monitor to provide instructions from the monitor to the sensor 10. The downstream monitor may then drive light to the appropriate emitter 16.

Figure 6:
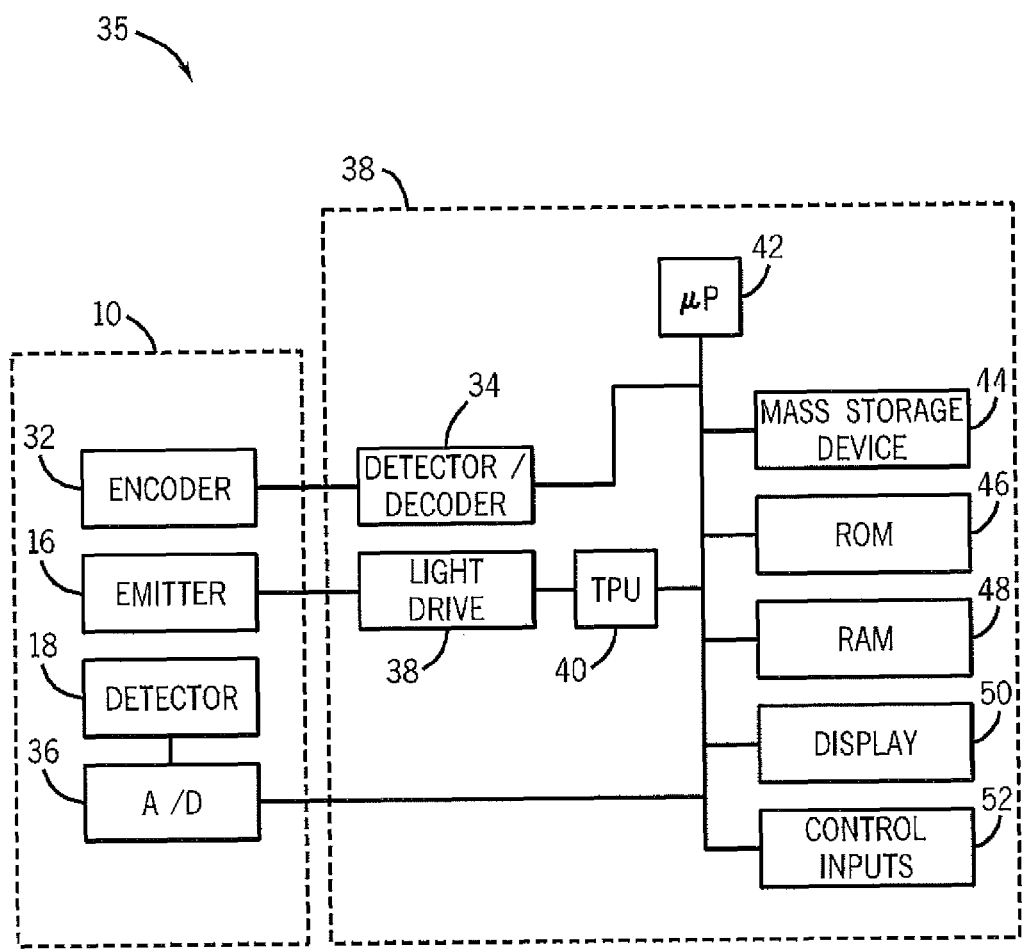
FIG. 6 is a block diagram of an exemplary medical monitoring system.

FIG. 6 is a block diagram of an embodiment of a system 36 that includes an exemplary sensor or sensor assembly 10 and an exemplary medical monitor 38 that may be configured to implement the embodiments of the present disclosure. Light from emitter 16 may pass into a blood perfused tissue, such as mucosal tissue in embodiments, and may be scattered, and then detected by detectors 18. A sensor assembly 10 containing an emitter 16 and a detectors 18 may also contain an encoder 32 which may be capable of providing signals indicative of the wavelength(s) and/or spacing from the detector/s 18 of light source 16 to allow the monitor 38 to select appropriate calibration coefficients for calculating the desired physiological parameter such as hematocrit or oxygen saturation. In embodiments, the encoder 32 may be configured to provide a signal related to the configuration of the sensor for a particular type of monitoring, such as mucosal tissue hematocrit or digit pulse oximetry. The encoder 32 may, in an embodiment, be a resistor located on an optical portion 14 of the sensor 10. The sensor 10 may also include an analog to digital converter 36 to digitize the signal generated by the detectors 18. In such an embodiment, the digitized sensor signal may be sampled at a high enough rate that the signal may be carried by a USB cable to a monitor 38. In certain embodiments, the USB signal may include time stamps or other information that may allow further analyzed by a processor 42.

The sensor 10 may include processing functionality. In an embodiment, the sensor 10 may include one or more "general-purpose" microprocessors, one or more special-purpose microprocessors and/or ASICS, or some combination thereof. The sensor 10 may also include circuitry and/or other structures that function as a RAM memory, and/or a time processing unit (TPU). In embodiments, the sensor 10 may also circuitry and/or other structures that provide the functionality of an amplifier and a switching circuit. These functions may allow signals to be sampled at the proper time, depending at least in part upon which of multiple light sources is activated, if multiple light sources are used. In addition, the sensor 10 may include circuitry and/or other structures that provide the functionality of additional amplification functions, and/or low pass filtering functions.

In an embodiment, the sensor 10 may be connected to a medical monitor 38. The monitor 38 may include a microprocessor 42 coupled to an internal bus. Also connected to the bus may be a RAM memory 48 and a display 50. A time processing unit (TPU) 40 may provide timing control signals to light drive circuitry 38, which controls when the emitter 16 is activated, and if multiple light sources are used, the multiplexed timing for the different light. The digital data may then be stored in RAM 46.

In an embodiment, the monitor 38 may be configured to receive digital signals from the sensor assembly 10. In an embodiment such a device may include a code or other identification parameter that may allow the monitor 38 to select an appropriate software or hardware instruction for processing the signal. In an embodiment, based at least in part upon the received signals corresponding to the light received by detectors 18, microprocessor 42 may calculate the oxygen saturation or hematocrit using various algorithms. These algorithms may require coefficients, which may be empirically determined, and may correspond to the wavelengths of light used. The algorithms may be stored in a mass storage device 44, a ROM 46, or a RAM 48, and may be accessed and operated according to microprocessor 42 instructions.

In an embodiment of a two-wavelength system, the particular set of coefficients chosen for any pair of wavelength spectra may be determined by a value indicated by the encoder 32 corresponding to a particular light source in a particular sensor assembly 10. In one embodiment, multiple resistor values may be assigned to select different sets of coefficients. In another embodiment, the same resistors are used to select from among the coefficients appropriate for an infrared source paired with either a near red source or far red source. For example, for pulse oximetry applications, the selection between whether the near red or far red set will be chosen can be selected with a control input from control inputs 52. Control inputs 52 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

In an embodiment, the sensor assembly 10 includes an emitter 16 and a detector 18 that may be of any suitable type. For example, the emitter 16 may be one or more light emitting diodes adapted to transmit one or more wavelengths of light in the red to infrared range, and the detectors 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics or light pipes 22. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multiphoton events or photoacoustic effects.

For pulse oximetry applications using either transmission or reflectance type sensors the oxygen saturation of the patient's arterial blood may be determined using two or more wavelengths of light, most commonly red and near infrared wavelengths. For hematocrit applications, techniques to determine hematocrit levels as provided in U.S. Pat. No. 6,606,509 to Schmitt et al., which is hereby incorporated by reference in its entirety for all purposes, may be employed. In embodiments, a hematocrit sensor 10 may include an emitter 16 configured to emit light at a wavelength in the range of about 500 nm to about 1000 nm or in a range of about 500 nm to about 700 nm. In embodiments, an emitter 16 may also emit light at a second wavelength at a wavelength in the range of 1250-1600 nm. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. In certain embodiments, determination of tissue water fraction may be incorporated into routines or algorithms to calculate hematocrit. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

In an embodiment, the sensor assembly 10 may include a "transmission type" sensor. Transmission type sensors include an emitter 16 and detectors 18 that are typically placed on opposing sides of the sensor site. If the sensor site is a fingertip, for example, the sensor assembly 10 is positioned over the patient's fingertip such that the emitter 16 and detector 18 lie on either side of the patient's nail bed. In other words, the sensor assembly 10 is positioned so that the emitter 16 is located on the patient's fingernail and the detectors 18 is located 180° opposite the emitter 16 on the patient's finger pad. In one embodiment, an attachment portion 12 may allow a sensor 10 to operate as a transmission sensor by capturing mucosal tissue between two prongs of a caliper-type configuration. A light pipe 22 in one prong of the caliper may deliver emitted light to the mucosal tissue and a light pipe 22 on an opposing side of the tissue may deliver light transmitted through the mucosal tissue to one or more detectors 18. During operation, the emitter 16 shines one or more wavelengths of light through the patient's fingertip and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor assembly 10 will perform in substantially the same manner.

Reflectance type sensors also operate by emitting light into the tissue and detecting the light that is transmitted and scattered by the tissue. However, reflectance type sensors include an emitter 16 and detector 18 that are typically placed on the same side of the sensor site. For example, a reflectance type sensor may be placed on a patient's fingertip or forehead such that the emitter 16 and detectors 18 lie side-by-side. Reflectance type sensors detect light photons that are scattered back to the detectors 18. A sensor assembly 10 may also be a "transflectance" sensor, such as a sensor that may subtend a portion of a baby's heel.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may to cover all modifications, equivalents, and alternatives falling within the spirit and scope of the disclosure as defined by the following appended claims

What is claimed is:

1. A sensor comprising:
an attachment portion comprising a curved structure configured to secure the sensor to a patient, wherein the attachment portion comprises a first light pipe configured to direct light into a mucosal tissue of the patient and comprises a second light pipe configured to receive light from the mucosal tissue of the patient; and
an optical portion comprising a light emitter and a light detector, wherein the attachment portion is configured to removably couple to the optical portion such that the light emitter is operatively coupled to the first light pipe and the detector is operatively coupled to the second light pipe.

2. The sensor, as set forth in claim 1, wherein a terminus of the first light pipe and a terminus of the second light pipe are spaced about 2 mm to about 2.5 mm from one another.

3. The sensor, as set forth in claim 1, wherein a terminus of the first light pipe and a terminus of the second light pipe are spaced such that the emitted light penetrates the mucosal tissue of the patient with a mean depth of penetration of less than 2 mm.

4. The sensor, as set forth in claim 1, wherein the attachment portion is configured to be nonadhesively applied to the mucosal tissue of the patient.

5. The sensor, as set forth in claim 1, wherein the curved structure comprises a hook configured to attach the sensor to a lip of the patient when the attachment portion is removably attached to the optical portion of the sensor.

6. The sensor, as set forth in claim 1, wherein the optical portion comprises a universal serial bus port.

7. The sensor, as set forth in claim 1, wherein the optical portion comprises an analog to digital converter configured to digitize a signal generated by the detector.

8. The sensor, as set forth in claim 1, wherein the sensor is configured to sense information related to oxygen saturation or hematocrit values.

9. The sensor, as set forth in claim 1, wherein the attachment portion comprises an adhesive portion configured to adhere to the patient's mucosal tissue.

10. The sensor, as set forth in claim 1, wherein the first light pipe and the second light pipe are spaced about 2 mm to about 2.5 mm from one another at a surface of the patient's mucosal tissue.

11. The sensor, as set forth in claim 1, wherein the first light pipe and the second light pipe are spaced such that the emitted light penetrates the patient's mucosal tissue with a mean depth of penetration of less than 2 mm.

12. A medical monitoring system comprising:
a medical monitor; and
a sensor configured to operatively couple to the monitor, the sensor comprising:
an attachment portion configured to be applied to a patient's mucosal tissue, wherein the attachment portion comprises a curved structure configured to secure the sensor to the patient near the patient's mucosal tissue, wherein the curved structure comprises a first light pipe configured to direct light into the patient's mucosal tissue and comprises a second light pipe configured to receive light from the patient's mucosal tissue;
an optical portion comprising a light emitter and a light detector, wherein the attachment portion is configured to removably couple to the optical portion such that the light emitter is operatively coupled to the first light pipe and the detector is operatively coupled to the second light pipe.

13. The system, as set forth in claim 12, wherein the detector is configured to detect light that has been directed through the second light pipe of the attachment portion.

14. The system, as set forth in claim 12, wherein a terminus of the first light pipe and a terminus of the second light pipe are spaced about 2 mm to about 2.5 mm from one another.

15. The system, as set forth in claim 12, wherein the monitor is coupled to the sensor by a universal serial bus port.

16. The system, as set forth in claim 12, wherein the optical portion comprises an analog to digital converter capable of digitizing a signal generated by the detector.

17. The system, as set forth in claim 12, wherein the sensor is capable of sensing information related to oxygen saturation or hematocrit values.

18. The system, as set forth in claim 12, wherein the first light pipe and the second light pipe are spaced about 2 mm to about 2.5 mm from one another such that the emitted light penetrates the patient's mucosal tissue with a mean depth of penetration of less than 2 mm.

19. A method comprising:
   removably coupling an attachment portion of a sensor to an optical portion of the sensor, wherein optical portion comprises an emitter and a detector, and wherein the attachment portion comprises a first light pipe and a second light pipe disposed within a curved structure, and wherein the emitter is operably coupled to the first light pipe and the detector is operably coupled to the second light pipe when the attachment portion and the optical portion of the sensor are removably coupled;
   securing the curved structure of the attachment portion to a patient such that the first and second light pipes of the attachment portion contact a mucosal tissue of the patient;
   determining a hematocrit level of the patient using the sensor.

20. The method, as set forth in claim 19, comprising directing light from the emitter to the mucosal tissue of the patient via the first light pipe and directing light from the mucosal tissue of the patient to the detector via the second light pipe, wherein the light penetrates the mucosal tissue with a mean penetration depth of less than about 2 mm.

\* \* \* \* \*